United States Patent
Govari et al.

(10) Patent No.: US 11,717,675 B2
(45) Date of Patent: Aug. 8, 2023

(54) PATIENT-SAFE ELECTROMECHANICAL SWITCHING FOR PACING WITH A CATHETER HAVING MULTIPLE ELECTRODES

(71) Applicant: Biosense Webster (Israel) Ltd., Yokneam (IL)

(72) Inventors: Assaf Govari, Haifa (IL); Vadim Gliner, Haifa (IL); Alon Boumendil, Givat Nili (IL); Ilya Sitnitsky, Nahariya (IL); Stanislav Katzir, Hadera (IL); Yehuda Algawi, Binyamina (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 488 days.

(21) Appl. No.: 16/530,702

(22) Filed: Aug. 2, 2019

(65) Prior Publication Data
US 2021/0031029 A1  Feb. 4, 2021

(51) Int. Cl.
| | | |
|---|---|---|
| *A61N 1/00* | (2006.01) | |
| *A61N 1/05* | (2006.01) | |
| *A61N 1/08* | (2006.01) | |
| *A61N 1/368* | (2006.01) | |
| *A61N 1/372* | (2006.01) | |

(52) U.S. Cl.
CPC ......... *A61N 1/0563* (2013.01); *A61N 1/0565* (2013.01); *A61N 1/08* (2013.01); *A61N 1/3686* (2013.01); *A61N 1/37247* (2013.01)

(58) Field of Classification Search
None
See application file for complete search history.

(56) References Cited

U.S. PATENT DOCUMENTS 2,264,746 A    12/1941  Ellwood
4,628,934 A *  12/1986  Pohndorf ............. A61N 1/3686
                                                                 607/27
(Continued)

FOREIGN PATENT DOCUMENTS

CN    202 191 600 U    4/2012

OTHER PUBLICATIONS

Advantages of reed switches in finished product designs. Reed Switch Developments Corp. (Jan. 16, 2016). Retrieved Jan. 26, 2022, from https://www.reedswitchdevelopments.com/advantages-of-reed-switches-in-finished-product-designs/ (Year: 2016).*

(Continued)

*Primary Examiner* — John R Downey
*Assistant Examiner* — Anant A Gupta
(74) *Attorney, Agent, or Firm* — Troutman Pepper Hamilton Sanders LLP (57) ABSTRACT

A pacing system includes a signal generator and an electromechanical switch. The signal generator is configured to generate a pacing signal. The electromechanical switch has a plurality of outputs that are configured to be coupled to a plurality of electrodes inserted into a heart of a patient, each output configured to deliver the pacing signal to a respective electrode. The electromechanical switch is configured to route the pacing signal to no more than a single selected one of the outputs at any given time, so as to pace the heart using no more than a single selected one of the electrodes.

22 Claims, 4 Drawing Sheets

(56) References Cited

U.S. PATENT DOCUMENTS

| | | | |
|---|---|---|---|
| 5,494,042 A * | 2/1996 | Panescu | A61B 5/339 |
| | | | 600/374 |
| 5,977,499 A | 11/1999 | Black et al. | |
| 6,107,699 A | 8/2000 | Swanson | |
| 6,262,647 B1 * | 7/2001 | Rogers | H01H 67/26 |
| | | | 335/206 |
| 6,421,567 B1 | 7/2002 | Witte | |
| 9,785,321 B2 | 10/2017 | Kurabayashi | |
| 2003/0000813 A1 * | 1/2003 | Roos | H01H 67/06 |
| | | | 200/1 R |
| 2011/0264159 A1 | 10/2011 | Spotnitz et al. | |

OTHER PUBLICATIONS

Advantages of reed switches in finished product designs. Reed Switch Developments Corp. (2016). Retrieved Jan. 26, 2022, from https://www.reedswitchdevelopments.com/advantages-of-reed-switches-in-finished-product-designs/ (Year: 2016).*
Extended European Search Report issued in European Patent Application No. 20 18 9011 dated Apr. 21, 2021.
Partial European Search Report issued in European Patent Application No. 20 18 9011 dated Jan. 13, 2021.
U.S. Pat. No. 447,918 A, Mar. 10, 1981, A. B. Strowger cited in EP SR's submitted herewith.

* cited by examiner

PATIENT-SAFE ELECTROMECHANICAL SWITCHING FOR PACING WITH A CATHETER HAVING MULTIPLE ELECTRODES

FIELD OF THE INVENTION

The present invention relates generally to electrophysiological mapping, and particularly to electromechanical switching for cardiac electrophysiological mapping.

BACKGROUND OF THE INVENTION

Invasive techniques for mapping electrophysiological properties of cardiac tissue cardiac may find use, mutatis mutandis, in electromechanical switching concepts that were generally proposed. An example of an electromechanical switch is brought in U.S. Pat. No. 5,977,499 that describes a linear slide selector switch for multiple channels for selecting between several switch positions. Specifically, there is a housing having a hinged door with a latch lock, the door rotates to a closed position and is held in a closed position by the latch lock. The housing also contains a slide and a printed circuit board. The printed circuit board has rows of contacts. A contactor is mounted to the slide. As the slide is moved linearly, electrical connections are made and broken on the printed circuit board.

As another example, U.S. Pat. No. 6,421,567 describes an implantable electrode arrangement which includes an electrode line with a plurality of electrically conductive surface regions in the region of the distal end of the electrode line for outputting electrical signals to a heart and/or for receiving signals from a heart. The electrode arrangement can be electrically connected by way of the electrode line to a cardio-electric device such as a defibrillator or cardiac pacemaker, which device receives electrical signals and/or outputs pulses. The electrode arrangement may include switching means, optionally being mechanical switching elements, which are of such an arrangement and configuration that the connection between individual ones of the electrically conducting surface regions and the cardio-electric device can be permanently switched on or off in the region of the electrode line.

SUMMARY OF THE INVENTION

An embodiment of the present invention provides a pacing system including a signal generator and an electromechanical switch. The signal generator is configured to generate a pacing signal. The electromechanical switch has a plurality of outputs that are configured to be coupled to a plurality of electrodes inserted into a heart of a patient, each output configured to deliver the pacing signal to a respective electrode. The electromechanical switch is configured to route the pacing signal to no more than a single selected one of the outputs at any given time, so as to pace the heart using no more than a single selected one of the electrodes.

In some embodiments, the electromechanical switch includes (a) a substrate patterned with multiple contacts arranged in an array, and each contact in the array is coupled to a respective output of the plurality of outputs, (b) a moving switch, which is configured to move over the array of contacts and to establish electrical contact with one contact only at any given time, and (c) a motor, which is configured to move the moving switch.

In some embodiments, the electromechanical switch further includes a screw that is configured to be rotated by the motor, and the moving switch of the electromechanical switch is coupled to the screw and is configured to move in a linear trajectory over a linear array of the contacts when the screw is rotated by the motor.

In some embodiments, the array of the contacts is arranged in a circular configuration, and the moving switch of the electromechanical switch is configured to move in a circular trajectory over the array of the contacts.

In an embodiment, the substrate of the electromechanical switch is made of a printed circuit board (PCB). In another embodiment, the motor of the electromechanical switch includes a stepper motor.

In an embodiment, the system further includes a processor, which is configured to apply a control loop that adaptively controls the motor to fine-tune a position of the moving switch, to optimize the electrical contact between the wheel and the contact. In another embodiment, the processor is configured to control the motor based on an electrocardiogram (ECG) sensed via the electrode associated with the contact.

In some embodiments, the moving switch includes a wheel that is configured to roll over the array of contacts. In an embodiment, the wheel is made of metal. In another embodiment, the wheel is made of an electrically conductive polymer. In yet another embodiment, the wheel is made of polymer and is disposed with electrically conducting strips.

In some embodiments, the electromechanical switch includes (a) a substrate disposed with multiple reed switches arranged in an array, wherein each reed switch in the array is coupled to a respective output of the plurality of outputs, (b) a moving switch comprising a magnet, which is configured to move over the array of reed switches and to cause only one reed switch to establish electrical contact at any given time, and (c) a motor, which is configured to move the moving switch.

In some embodiments, the pacing system further includes a processor, which is configured to command the pacing generator to generate the pacing signal and command the electromechanical switch to route the pacing signal according to a prespecified pacing protocol.

In some embodiments, the pacing signal is unipolar. In other embodiments, the pacing signal is bipolar, and the pacing system includes an additional electromechanical switch to form a double electromechanical switch together with the electromechanical switch. The dual electromechanical switch is configured to route the bipolar pacing signal to no more than a selected pair of the outputs at any given time, so as to pace the heart bipolarly using no more than a selected pair of the electrodes.

In an embodiment, the dual electromechanical switch includes (a) a substrate patterned with multiple contacts arranged in a first array, each contact in the first array is coupled to a respective output of the plurality of outputs, and multiple contacts arranged in a second array, and wherein each contact in the second array is coupled to a respective output of the plurality of outputs, (b) a first moving switch, which is configured to move over the first array of contacts and to establish electrical contact with one contact only of the first array at any given time, (c) a second moving switch, which is configured to move over the second array of contacts and to separately establish electrical contact with one contact only of the second array at any given time, and (d) one or more motors, which are configured to move the first moving switch and the second moving switch independently of each other.

In an embodiment, the first array of contacts and the second array of contacts of the dual electromechanical switch are spatially separated in space. In another embodiment, the first array and the second array of contacts are concentric circular arrays. In an embodiment, the first array and the second array of contacts are vertically overlaid over one another.

In some embodiments, the dual electromechanical switch includes (a) a substrate patterned with multiple reed switches arranged in a first array, wherein each reed switch in the first array is coupled to a respective output of the plurality of outputs, and multiple reed switches arranged in a second array, and wherein each reed switch in the second array is coupled to a respective output of the plurality of outputs, (b) a first moving switch comprising a magnet, which is configured to move over the first array of reed switches and to cause only one reed switch of the first array to establish electrical contact at any given time, (c) a second moving switch comprising a magnet, which is configured to move over the second array of reed switches and to separately cause only one reed switch of the second array to establish electrical contact at any given time, and (d) one or more motors, which are configured to move the first moving switch and the second moving switch independently of each other.

There is additionally provided, in accordance with an embodiment of the present invention, a method for pacing a heart, the method including generating a pacing signal. Using an electromechanical switch having a plurality of outputs that are coupled to a plurality of electrodes inserted into the heart for, each output configured to deliver the pacing signal to a respective electrode, the pacing signal is routed to no more than a single selected one of the outputs at any given time, so as to pace the heart using no more than a single selected one of the electrodes.

There is further provided, in accordance with an embodiment of the present invention, a manufacturing method, including patterning a substrate with multiple contacts arranged in an array. A moving switch is provided, which is configured to move over the array and to establish electrical contact with one contact only at any given time. One or more motors are provided, which are configured to move the moving switch.

There is additionally provided, in accordance with an embodiment of the present invention, a manufacturing method, including patterning a substrate with multiple contacts arranged in a first array, and multiple contacts arranged in a second array. A first moving switch is provided, which is configured to move over the first array and to establish electrical contact with one contact only of the first array at any given time. A second moving switch is provided, which is configured to move over the second array and to separately establish electrical contact with one contact only of the second array at any given time. One or more motors are coupled, which are configured to move the first moving switch and the second moving switch independently of each other.

The present invention will be more fully understood from the following detailed description of the embodiments thereof, taken together with the drawings in which:

DETAILED DESCRIPTION OF EMBODIMENTS

Overview

In delivering signals to the heart using a catheter, such as during cardiac pacing session of an electrophysiological (EP) mapping procedure, it is medically critical to avoid incorrect delivery. Thus, delivery systems for a catheter with multiple electrodes, such as those on a diagnostic EP catheter, must avoid using semiconductor electrical devices in the delivery signal path, since semiconductors may not have sufficient electrical isolation between adjacent channels, as well as the possibility of electrical breakdown in the semiconductor of a particular channel.

Embodiments of the present invention that are described hereinafter provide pacing systems and pacing methods that are patient safe, for use with catheters having multiple electrodes.

In some embodiments, a pacing system is provided, that uses body surface patches as return electrodes in a unipolar pacing layout. The pacing system comprises (a) a signal generator configured to generate a pacing signal, and (b) an electromechanical switch having a plurality of outputs coupled to a plurality of electrodes inserted into a heart of a patient, each output configured to deliver the pacing signal to a respective electrode, wherein the electromechanical switch is configured to route the pacing signal to no more than a single selected one of the outputs at any given time, so as to pace the heart using no more than a single selected one of the electrodes. The disclosed electromechanical switch prevents any possibility of inter-electrode leakage. Even if the system breaks down (e.g., the motor fails) there is no possibility of inter-channel leakage or of delivery of current to the wrong channel.

In an embodiment, the electromechanical switch comprises (i) a substrate patterned with multiple contacts arranged in an array, where each contact in the array is coupled to a respective output of the plurality of outputs, (ii) a moving switch, which is configured to move over the array of contacts and to establish electrical contact with one contact only at any given time, and (iii) a motor, which is configured to move the moving switch.

In the context of the disclosed inventions, a moving switch may: roll over the contacts by a wheel rolling over the contacts, or slide over the contacts by having a slidable contacting element. Both the wheel and the slidable contacting element are electrically conductive. In some embodiment, the wheel is made of metal, in other embodiments the wheel is made of a polymer that includes conductive element. A conductive element may cause the bulk of the wheel to conduct electricity or be a pattern of conducting material disposed on the surface of the polymer wheel. Examples of polymers that can be used include various types of rubbers.

In some embodiments, a non-contact moving electromechanical switching is implemented, as described below, by using an array of reed switches (i.e., an array of electrical switches operated by an applied magnetic field). A reed switch is described in U.S. Pat. No. 2,264,746 (granted Dec. 2, 1941).

In some embodiments the pacing system is configured to pace with a bipolar signal, and comprises an additional electromechanical switch which moves independently of the first switch. The resulting dual electromechanical switch is configured to route the bipolar pacing signal to no more than a first and second single selected two of the outputs at any given time, so as to pace the heart bipolarly using no more than single selected first and second electrode of the electrodes. Typically, the dual electromechanical switch is realized on a same substrate as, for example, a double linear, concentric or side by side circular layouts, as described below.

In some embodiments, the dual electromechanical switch comprises (a) a substrate patterned with multiple contacts arranged in a first array, wherein each contact in the first array is coupled to a respective output of the plurality of outputs, and multiple contacts arranged in a second array, and wherein each contact in the second array is coupled to a respective output of the plurality of outputs, (b) a first moving switch, which is configured to move over the first array of contacts and to establish electrical contact with one contact only of the first array at any given time, (c) a second moving switch, which is configured to move over the second array of contacts and to separately establish electrical with one contact only of the second array at any given time, and (d) one or more motors which are configured to move the first moving switch and the second moving switch independently of each other. The two arrays are spatially separated in space, e.g., laterally and/or vertically.

In some embodiments, the disclosed electromechanical switch may switch a pacing signal from the signal generator between, for example, more than hundred receiving electrodes of a catheter. A delivery system, such as a cardiac EP mapping system using the disclosed electromechanical relaying, can be either in an "off" or "on" state, and it does not pose the problem of incorrect delivery of unipolar or bipolar signals if the electromechanical switch breaks down, as described below.

In an embodiment, moving switches of the dual electromechanical switch are each constrained to move in a linear trajectory by being coupled to a lead screw that is rotated by a processor-controlled motor, such as a stepper motor. In another embodiment, the moving switches of the electromechanical switch are each constrained to move in a circular trajectory by being rotated by a stepper motor, as described below. According to the type of motion (linear or circular), arrays of electrode contacts are formed on a line or a circle.

In some embodiments, the contact arrays are formed on a substrate, such as a printed circuit board (PCB), and the stepper motor is rotated until a moving contact of a moving switch aligns with the selected contact. The sizes of the moving contacts and array contacts are selected such that, regardless of the moving switch position, only one contact in each array can be connected at any given time.

In some embodiments, electrodes from two or more catheters may be connected to a single dual electromechanical switch, for example, for pacing with unipolar signals with one catheter and sensing resulting EP signals with the other catheter.

The disclosed pacing systems may comprise a processor, which is configured to command the pacing generator to generate the pacing signals and command the electromechanical switch routing the pacing signal according to a prespecified pacing protocol.

The disclosed electromechanical switching techniques thus provides a patient safe and flexible solution to enable either unipolar or bipolar pacing using catheters comprising multiple electrodes.

System Description

Figure 1:
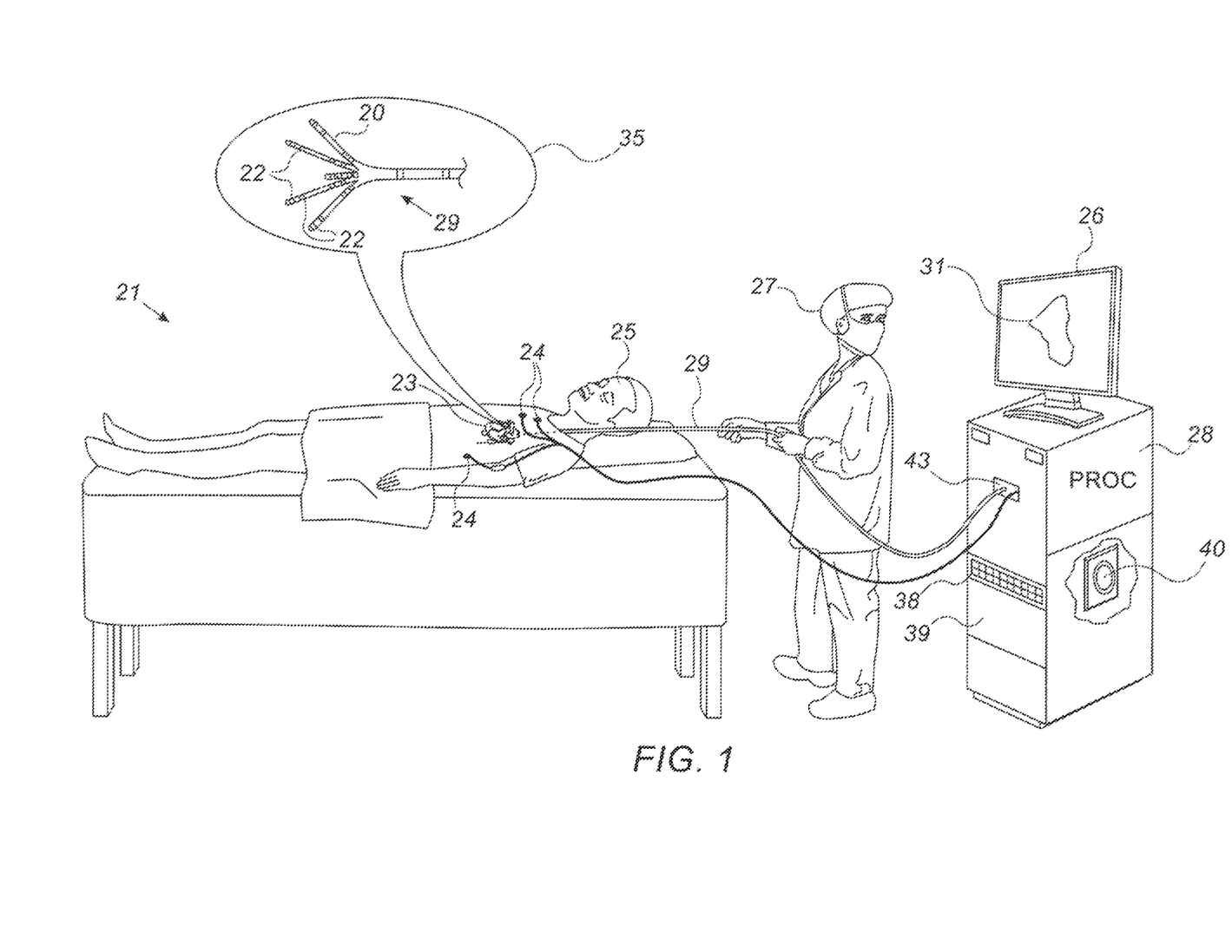
FIG. 1 is a schematic, pictorial illustration of an electrophysiological (EP) mapping system comprising a concentric circular electromechanical switch, in accordance with an embodiment of the present invention.

FIG. 1 is a schematic, pictorial illustration of an electrophysiological (EP) mapping system 21 comprising a concentric circular electromechanical switch 40, in accordance with an embodiment of the present invention. Electromechanical switch 40 is described in FIG. 2B. As shown, a physician 27 uses an EP mapping catheter 29 to pace a heart 23 of a patient 25. Catheter 29 comprises, at its distal end, as seen in inset 35, multiple arms 20, which may be mechanically flexible, to each of which are coupled multiple electrodes 22.

During the pacing procedure, electrodes 22 inject to, and acquire signals from, the tissue of heart 23. A processor 28 receives the acquired signals via an electrical interface 43, and uses information contained in these signals to construct an EP map 31 of at least part of wall tissue of heart 23 of patient 25. During and/or following the procedure, processor 28 may display EP map 31 on a display 26.

In some embodiments, system 21 variably paces heart by a processor 28 instructing a circular electromechanical switch 40 to route (i.e., switch) bipolar signals, which a pacing signal generator 39 generates. The bipolar signals are outputted to a plurality of electrodes 22 by a plurality of outputs 38 of electromechanical switch 40 that electrodes 22 are coupled to. Electromechanical switch 40 switches the outputted signals between multiple different pairs of electrodes 22. System 21 may measure resulting electrical activity of a heart 23 using some or all of electrodes 22.

In some embodiments, to pace heart 23 in a bipolar manner via sequential selection of numerous electrode-pairs 22, processor 28 may apply a predefined automatic stimulation-routing protocol. Using the protocol, processor 28 commands concentric electromechanical switch 40 to route (i.e., to switch) between different electrode-pairs 22 according to a certain predetermined sequence. An example of a procedure that may benefit from automatic stimulation-routing is pulmonary vein isolation validation.

During pacing, the respective locations of electrodes 22 are tracked. The tracking may be performed, for example, using a Carto3® system produced by Biosense-Webster (Irvine, Calif.). Such a system measures impedances between electrodes 22 and a plurality of external conducting patches 24 that are coupled to the body of patient 25; for example, three external conducting patches 24 may be coupled to the patient's chest, and another three external electrodes may be coupled to the patient's back. For ease of illustration, only the chest electrodes are shown. The disclosed pacing system may use conducting patches 24 as return electrodes in a unipolar pacing layout.

The example illustration shown in FIG. 1 is chosen purely for the sake of conceptual clarity. Other sensing geometry types, such as that in the Lasso® Catheter (produced by Biosense Webster Inc.) may also be employed.

Processor 28 uses software stored in a memory 42 to operate system 21. The software may be downloaded to processor 28 in electronic form, over a network, for example, or it may, alternatively or additionally, be provided and/or stored on non-transitory tangible media, such as magnetic, optical, or electronic memory. In particular, processor 28 runs a dedicated algorithm that enables processor 28 to perform the functions described above.

Figure 2A:
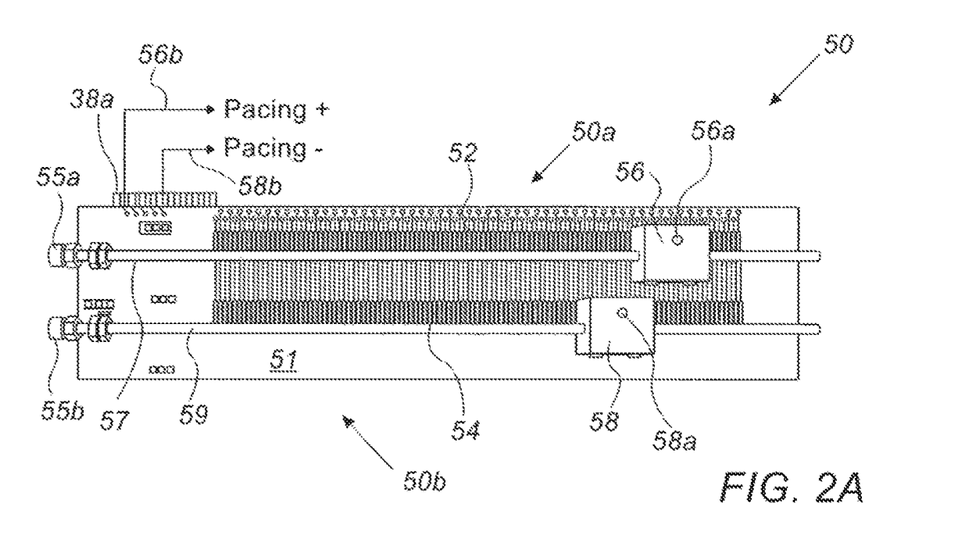
FIGS. 2A-2C are schematic, top view illustrations of a double linear electromechanical switch, of the concentric circular electromechanical switch of FIG. 1, and of a side-by-side circular electromechanical switch layout, respectively, in accordance with embodiments of the present invention.
Figure 2B:
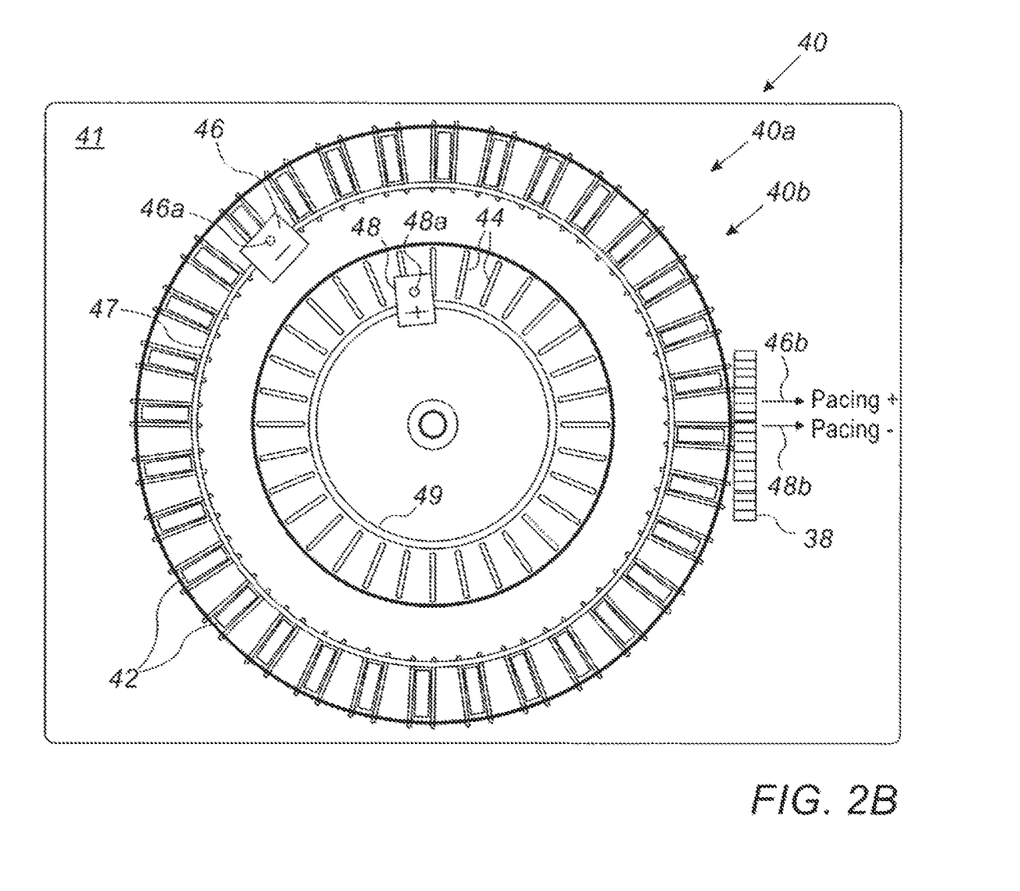
Figure 2C:
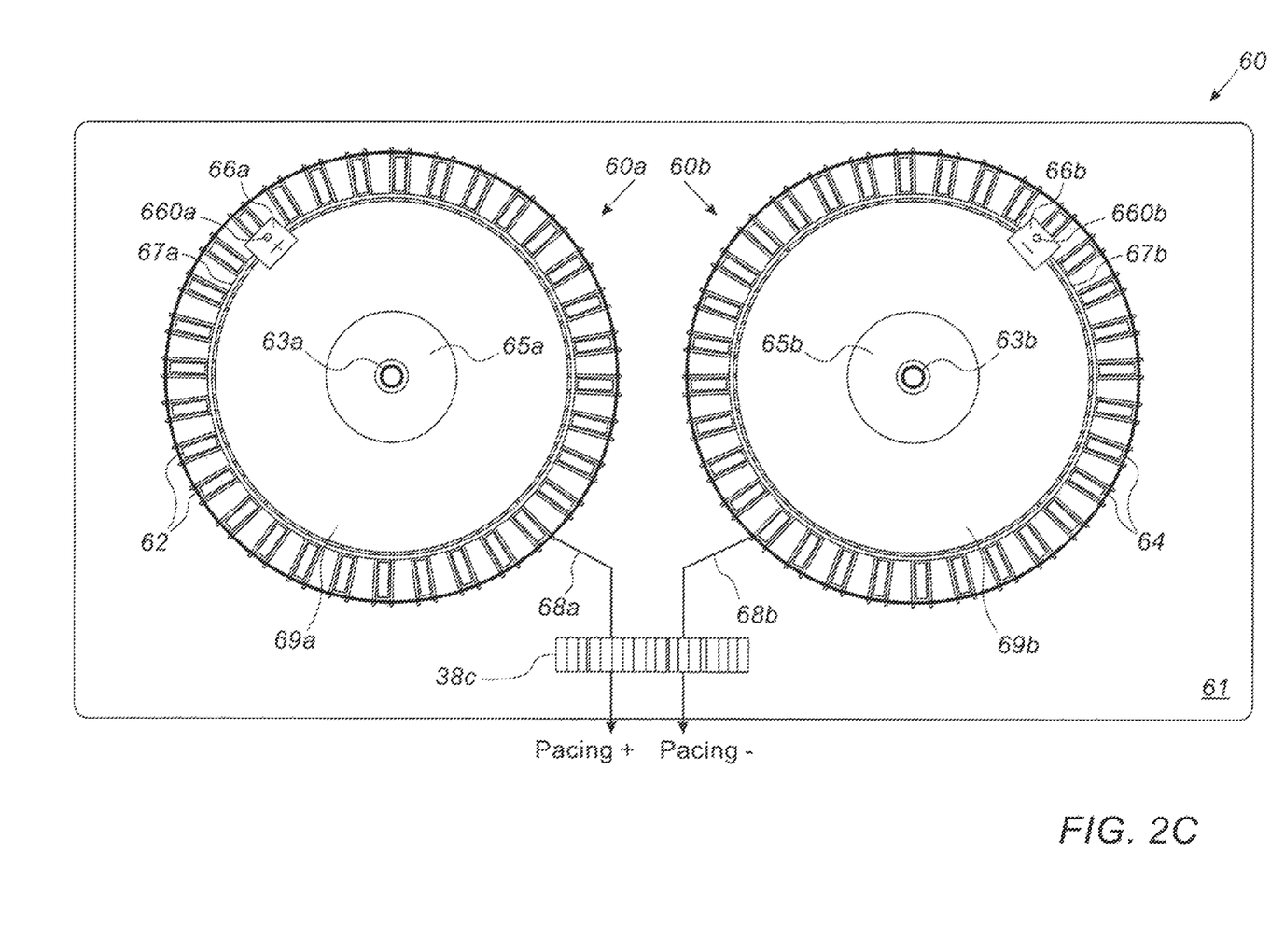

Patient-Safe Mechanical Switching for Pacing with a Catheter Having Multiple Electrodes FIGS. 2A-2C are schematic, top view illustrations of a dual linear electromechanical switch 50, of concentric circular electromechanical switch 40 of FIG. 1, and of a side-by-side circular electromechanical switch 60 layout, respectively, in accordance with embodiments of the present invention. The disclosed electromechanical dual switches are configured to route bipolar pacing signals.

As seen in FIG. 2A, dual linear electromechanical switch 50 comprises two linear contact arrays 50a and 50b that are aligned in parallel to each other. First linear array 50a comprises contacts 52 and, second linear array 50b comprises contacts 54. The electrodes are disposed on a substrate made of a printed circuit board (PCB) 51.

Moving switches 56 and 58 are each constrained to move in a linear trajectory between contacts 52 and between contacts 54 by being coupled to lead screws 57 and 59, respectively. Each of screws 57 and 59 is independently rotated by stepper motors 55a and 55b, respectively. First moving switch 56 comprises a moving contact 56a, and second moving switch 58 comprises a moving contact 58a, where moving contacts 56a and 58a independently move on contact arrays 50a and 50b, respectively. Only a single contact at each of arrays 50a and 50b can be connected to a moving contact at any given time, which ensures electrical isolation between adjacent channels of system 21 used for pacing heart 23.

Moving contacts 56a and 58a are connected to a pacing signal source included on system 21 (connections and source not shown). The bipolar signals are outputted to a plurality of electrodes 22 (seen in FIG. 1) by a plurality of outputs 38a of electromechanical switch 50 that electrodes 22 are coupled to. Electromechanical switch 50 outputs the pacing signal to the selected electrodes in catheter 29 via leads 56b and 58b of switch 50, respectively.

As seen in FIG. 2B, concentric circular electromechanical switch 40 comprises a first, outer, circular array 40a of contacts 42 and a second, inner, circular array 40b of contacts 44, disposed on a substrate made of a printed circuit board (PCB) 41. The two circular arrays are concentrically aligned.

Moving switches 46 and 48 are each constrained to move in a circular trajectory between electrode contacts, by being coupled to circular rails 47 and 49, respectively. Each of moving switches 46 and 48 are coupled to a stepper motor (an exemplary coupling mechanism and a stepper motor are shown in FIG. 2C) that rotates each moving switch over its respective circular rail. First moving switch 46 comprises a moving contact 46a, and second moving switch 48 comprises a moving contact 48a, that can respectively and independently move on contact arrays 40a and 40b. Only a single contact at each array can be connected to a moving contact at any given time, to ensure electrical isolation between adjacent channels of system 21 used for pacing heart 23.

Moving contacts 46a and 48a are connected to a pacing signal source included on system 21 (connections and source not shown). The bipolar signals are outputted to a plurality of electrodes 22 (seen in FIG. 1) by a plurality of outputs 38 of electromechanical switch 40 that electrodes 22 are coupled to. Electromechanical switch 40 outputs the pacing signal to the selected electrodes in catheter 29 via leads 46b and 48b of switch 40, respectively.

As seen in FIG. 2C, side-by-side circular electromechanical switch 60 comprises a first circular array 60a of contacts 62, which is disposed side-by-side to a second circular array 60b of contacts 64. Both arrays are disposed on a substrate made of a printed circuit board (PCB) 61.

Moving switches 66a and 66b are each constrained to move in a circular trajectory between contacts 62 and between contacts 64 by being coupled to rails 67a and 67b, respectively, where rails 67a and 67b are similar to rail 47 of FIG. 2B. Each of moving switches 66a and 66b are coupled to stepper motors 65a and 65b, respectively, by a coupling mechanism comprising respective discs 69a and 69b, via respective shafts 63a and 63b, where each shaft rotates each disc so as to rotate each moving switch over its respective circular rail.

A first moving switch 66a comprising a moving contact 660a, and a second moving switch 66b comprising a moving contact 660b, can respectively move on contact arrays 60a and 60b. Only a single contact at each array can be connected to a moving contact at any given time, to ensure electrical isolation between adjacent channels of system 21 used for pacing heart 23.

Moving contacts 660a and 660b are connected to a pacing signal source included on system 21 (electrical connections and signal source not shown). The bipolar signals are outputted to a plurality of electrodes 22 (seen in FIG. 1) by a plurality of outputs 38c of electromechanical switch 60 that electrodes 22 are coupled to. Electromechanical switch 60 outputs the pacing signal to the selected electrodes in catheter 29 via leads 68a and 68b of switch 60.

The top view illustrations shown in FIG. 2 are brought by way of example, and are simplified for the sake of conceptual clarity. For example, motion mechanisms are sketched with minimal detail.

Figure 3:
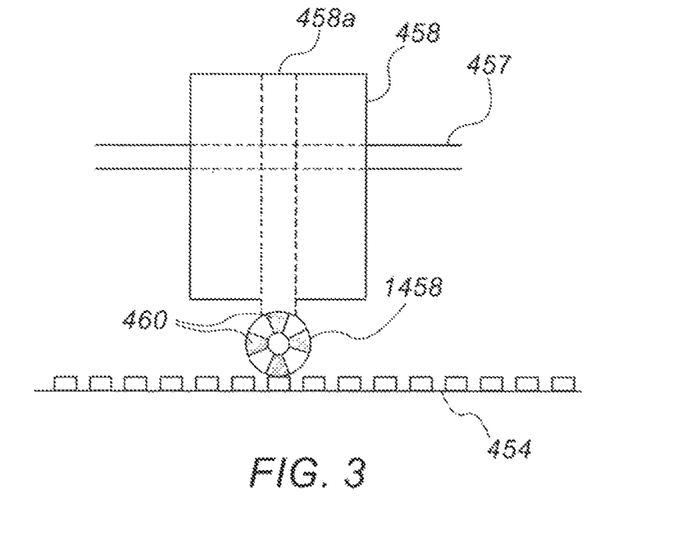
FIG. 3 is a schematic, side view illustration of a wheeled moving switch of the electromechanical switches of FIGS. 2A-2C, in accordance with an embodiment of the present invention.

FIG. 3 is a schematic, side view illustration of a wheeled moving switch of the electromechanical switches of FIGS. 2A-2C, in accordance with an embodiment of the present invention. As seen, a moving switch 458 comprises a moving contact 458a that is rolled, using an electrically conducting wheel 1458, over an array of contacts 454. Moving switch 458 is moved by a screw 457 that is rotated by a motor (such as by stepper motors 55a and 55b of FIG. 2A).

In some embodiments, wheel 1458 is made metal. In other embodiments wheel 1458 is made of an electrically conducting polymer, such as an electrically conducting rubber. Using rubber may extend the lifetime of the mechanical switch, by preventing erosion of the pads, such as due to metal to metal friction and metal to metal scratching. Using rubber may also improve the mechanical contact between wheel 1458 and each of contacts 454, e.g., by accommodating changing topography of the contacts.

In some embodiments, the polymer wheel is disposed with conductive strips 460 to establish an electrical contact separately with each of contacts 454, as wheel 1458 is rolling. For that, conductive strips 460 (e.g., gold strips) cover portion of circumference of the wheel. The wheel itself serves as a mechanical absorber and eliminate the high friction with the PCB pads, and accommodates for vertical miss alignments between moving switch 458 and the PCB for better mechanical contact. Strips 460 are drawn in FIG. 3 as sectors of a circle yet could have other suitable patterns.

In some embodiments, in order to establish firm electrical contact between wheel 1458 and a contact 454, processor 28 applies a control loop that adaptively controls the motor to fine-tune a position of moving switch 458 (e.g., by the wheel moving forwards\backwards). Processor 28 is configured to control the motor based on an electrocardiogram (ECG) sensed via the electrode associated with the contact. For example, when the system senses, via the respective electrode, an ECG of acceptable quality according to a prespecified criterion (e.g., of large enough signal), processor 28 determines that a good electrical contact was achieved for switching between wheel 1458 on contact 454. Using ECG to control quality of contact may assist in cases where, for example, a dust particle on a contact degrades the electrical contact, since the area of contact is small (e.g., a tangent line of a circle).

Figure 4:
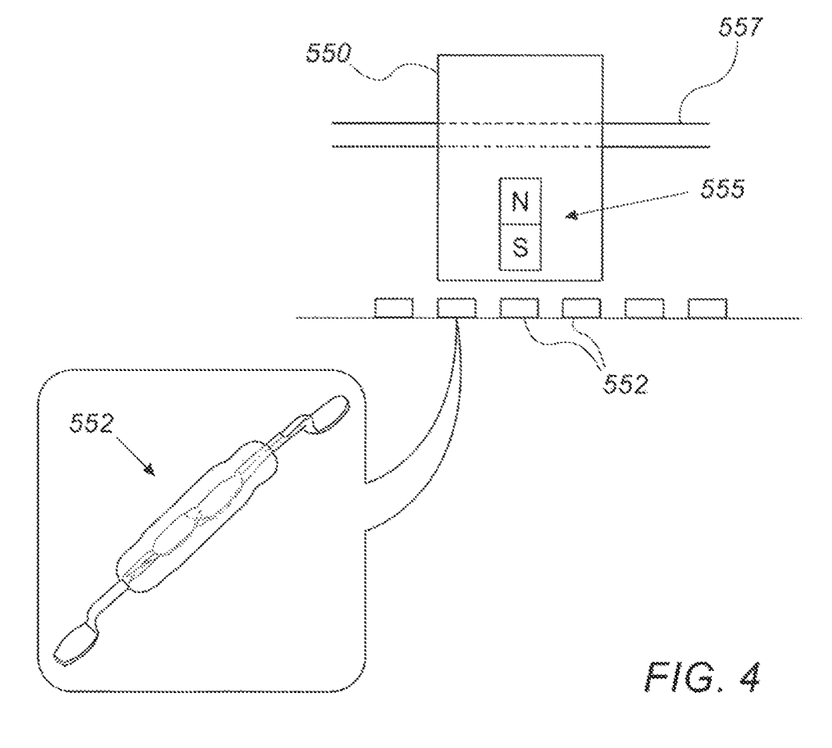
FIG. 4 is a schematic, illustration of a reed switch layout of the electromechanical switches of FIGS. 2A-2C, in accordance with an embodiment of the present invention.

FIG. 4 is a schematic, illustration of a reed switch layout of the electromechanical switches of FIGS. 2A-2C, in accordance with an embodiment of the present invention. As seen, there is a gap, i.e., no mechanical contact between a moving switch 550 and an array of reed switches 552. Instead, wherever moving switch 550 is located over a reed switch 552, a magnet 555, such as a fixed magnet, inside moving switch 550 causes the normally open reed switch 552 to close and pass the pacing signal. Moving switch 550 is moved by a screw 557 that is rotated by a motor (such as by stepper motors 55a and 55b of FIG. 2A).

As seen in the inset, a reed switch typically has two "sticks" in normally open mode and with the magnet these "sticks" can be connected. Using reed switches may extends the life of the disclosed pacing switch by eliminating issues of mechanical ware (e.g., destruction of PCB pads due to friction with a movable switch).

In some embodiments, magnet 555 is an electromagnet, that is kept off when moved over reed switches not intended to make contact. The electromagnet is thus operated only when it is positioned above a target reed switch, to close the circuit at the intended channel. More options are possible to avoid activation of wrong reed switches: for example, magnet 555 may be held flipped horizontally while moving over the array and be flipped vertically only over the target reed switch. Other means, such as disconnecting the reed switch using logic are also possible.

The illustration in FIG. 4 is brought by way of example. Other embodiments are possible using the reed switches, for example, by using an electromagnet instead of a fixed magnet to switch the reed switches.

Although the embodiments described herein mainly address medical applications, the methods and systems described herein can also be used in other applications, such as in electrical switches, control circuits, and communication switches.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A pacing system, comprising:
a signal generator configured to generate a pacing signal; and
an electromechanical switch having:
    a substrate patterned with a plurality of contacts arranged in a circular array, wherein each contact in the circular array is configured to be in electrical communication with an electrode of a plurality of electrodes inserted into a heart of a patient, each contact of the plurality of contacts being configured to deliver the pacing signal to a respective electrode of the plurality of electrodes; and
    a moving switch attached to a circular rail and configured to move along the circular rail in a circular trajectory over the plurality of contacts and to establish electrical contact with one contact only at any given time,
wherein the electromechanical switch is configured to route the pacing signal to no more than a single selected one of the contacts at any given time, so as to pace the heart using no more than a single selected one of the electrodes.

2. The pacing system according to claim 1, wherein the electromechanical switch further comprises:
a motor, which is configured to move the moving switch.

3. The pacing system according to claim 1, wherein the substrate of the electromechanical switch is made of a printed circuit board (PCB).

4. The pacing system according to claim 2, wherein the motor of the electromechanical switch comprises a stepper motor.

5. The pacing system according to claim 2, wherein the moving switch comprises a wheel that is configured to roll over the array of contacts.

6. The pacing system according to claim 5, and comprising a processor, which is configured to apply a control loop that adaptively controls the motor to fine-tune a position of the moving switch, to optimize the electrical contact between the wheel and the contact.

7. The pacing system according to claim 6, wherein the processor is configured to control the motor based on an electrocardiogram (ECG) sensed via the electrode associated with the contact.

8. The pacing system according to claim 5, wherein the wheel is made of metal.

9. The pacing system according to claim 5, wherein the wheel is made of an electrically conductive polymer.

10. The pacing system according to claim 5, wherein the wheel is made of polymer and is disposed with electrically conducting strips.

11. The pacing system according to claim 1, wherein the plurality of contacts comprises multiple reed switches, wherein each reed switch is coupled to a respective contact of the plurality of contacts,
    wherein the moving switch comprises a magnet, which is configured to move over the reed switches and to cause only one reed switch to establish electrical contact at any given time, and
    wherein the pacing system further comprises a motor configured to move the moving switch.

12. The pacing system according to claim 1, and comprising a processor, which is configured to command the pacing generator to generate the pacing signal and command the electromechanical switch to route the pacing signal according to a prespecified pacing protocol.

13. The pacing system according to claim 1, wherein the pacing signal is unipolar.

14. The pacing system according to claim 1, wherein the pacing signal is bipolar, and wherein the pacing system comprises an additional electromechanical switch to form a dual electromechanical switch together with the electromechanical switch, wherein the dual electromechanical switch is configured to route the bipolar pacing signal to no more than a selected pair of the contacts at any given time, so as to pace the heart bipolarly using no more than a selected pair of the electrodes.

15. The pacing system according to claim 14, wherein the substrate is a substrate patterned with (1) multiple contacts arranged in a first circular array, wherein each contact in the first circular array is configured to be in electrical communication with a respective electrode of the plurality of electrodes, and (2) multiple contacts arranged in a second circular array, and wherein each contact in the second circular array is configured to be in electrical communication with a respective electrode of the plurality of electrodes,
wherein the moving switch is a first moving switch attached to a first circular rail and configured to move along the first circular rail over the first circular array of contacts and to establish electrical contact with one contact only of the first circular array at any given time,
wherein the dual electromechanical switch further comprises:
a second moving switch attached to a second circular rail and configured to move along the second circular rail over the second circular array of contacts and to separately establish electrical contact with one contact only of the second circular array at any given time; and
a first motor configured to move the first moving switch independent of the second moving switch; and
a second motor configured to move the second moving switch independent of the first moving switch.

16. The pacing system according to claim 15, wherein the first array of contacts and the second array of contacts of the dual electromechanical switch are spatially separated in space.

17. The pacing system according to claim 15, wherein the first array and the second array of contacts are concentric circular arrays.

18. The pacing system according to claim 15, wherein the first array and the second array of contacts are vertically overlaid over one another.

19. The pacing system according to claim 14, wherein the substrate is a substrate patterned with (1) multiple reed switches arranged in a first circular array, wherein each reed switch in the first circular array is coupled to a respective output of the plurality of outputs, and (2) multiple reed switches arranged in a second circular array, and wherein each reed switch in the second circular array is coupled to a respective contact of the plurality of contacts,
wherein the moving switch comprises a first moving switch comprising a magnet, which is configured to move over the first circular array of reed switches and to cause only one reed switch of the first circular array to establish electrical contact at any given time,
wherein the pacing system further comprises:
a second moving switch comprising a magnet, which is configured to move over the second circular array of reed switches and to separately cause only one reed switch of the second circular array to establish electrical contact at any given time; and
a first motor configured to move the first moving switch independent of the second moving switch; and
a second motor configured to move the second moving switch of the first moving switch.

20. A method for pacing a heart, the method comprising:
generating a pacing signal; and
using an electromechanical switch having:
a substrate patterned with a plurality of contacts arranged in a circular array, wherein each contact in the circular array is coupled to a plurality of electrodes inserted into the heart; and
a moving switch attached to a circular rail and configured to move along the circular rail in a circular trajectory over the plurality of contacts and to establish electrical contact with one contact only at any given time,
wherein each contact is configured to deliver the pacing signal to a respective electrode so as to pace the heart using no more than a single selected one of the electrodes.

21. A manufacturing method, comprising:
patterning a substrate with multiple contacts arranged in a circular array;
providing a moving switch attached to a circular rail, which is configured to move along the circular rail in a circular trajectory over the circular array and to establish electrical contact with one contact only at any given time; and
providing one or more motors, which are configured to move the moving switch.

22. A manufacturing method, comprising:
patterning a substrate with multiple contacts arranged in a first circular array, and multiple contacts arranged in a second circular array;
providing a first moving switch mechanically coupled to a first circular rail, which is configured to move over the first circular array and to establish electrical contact with one contact only of the first circular array at any given time;
providing a second moving switch mechanically coupled to a second circular rail, which is configured to move over the second circular array and to separately establish electrical contact with one contact only of the second circular array at any given time; and
coupling a first motor to the first moving switch, the first motor configured to move the first moving switch independent of the second moving switch; and
coupling a second motor to the second moving switch, the second motor configured to move the second moving switch independent of the first moving switch.

* * * * *